(12) United States Patent
Alpert

(10) Patent No.: US 10,687,683 B2
(45) Date of Patent: Jun. 23, 2020

(54) WASHING OR WASHING/STERILIZING AND DRYING OR DRYING/STERILIZING WITH OPTIONAL INDEPENDENT STERILIZATION APPARATUS WITH ROBOTIC ARMS

(71) Applicant: Martin A. Alpert, Beachwood, OH (US)

(72) Inventor: Martin A. Alpert, Beachwood, OH (US)

( * ) Notice: Subject to any disclaimer, the term of this patent is extended or adjusted under 35 U.S.C. 154(b) by 296 days.

(21) Appl. No.: 15/467,018

(22) Filed: Mar. 23, 2017

(65) Prior Publication Data

US 2017/0273534 A1    Sep. 28, 2017

Related U.S. Application Data

(60) Provisional application No. 62/312,752, filed on Mar. 24, 2016.

(51) Int. Cl.
*A61L 2/00* (2006.01)
*F26B 19/00* (2006.01)
(Continued)

(52) U.S. Cl.
CPC ............ *A47L 15/0021* (2013.01); *A47K 7/04* (2013.01); *A47L 15/0044* (2013.01); *A47L 15/0047* (2013.01); *A47L 15/0063* (2013.01); *A47L 15/0089* (2013.01); *A47L 15/16* (2013.01); *A47L 15/18* (2013.01); *A47L 15/22* (2013.01); *A47L 15/4257* (2013.01);
(Continued)

(58) Field of Classification Search
CPC . A61L 2/07; A61L 2/24; A61L 2/0088; A47L 15/00; A47L 17/00; A47L 19/00; A47L 21/00; B08B 2203/00; B05B 11/00

USPC ....... 422/261, 292, 295, 297, 299, 300, 302; 134/58 D, 61, 84, 94.1, 103.2, 105, 172; 34/209
See application file for complete search history.

(56) References Cited

U.S. PATENT DOCUMENTS 7,604,012 B2 * 10/2009 Alpert ................. A47L 15/0002
134/58 D
8,340,820 B2    12/2012 Nair
(Continued)

FOREIGN PATENT DOCUMENTS

EP    0 216 482 A1    4/1987

*Primary Examiner* — Jill A Warden
*Assistant Examiner* — Monzer R Chorbaji
(74) *Attorney, Agent, or Firm* — Renner, Otto, Boisselle & Sklar, LLP

(57) ABSTRACT

A washing and drying unit configured to perform at least one of washing, drying, and sterilizing, or any combination thereof includes at least one sensor configured to determine a dimension and/or shape of the object, a washing and/or sterilizing apparatus and a drying and/or sterilizing apparatus configured to direct at least one apparatus or spray of a washing and/or sterilizing or a drying and/or sterilizing fluid to the object, at least one robot arm connected to at least one of the apparatuses, and a controller operable to orient and move the at least one robot arm. A separate sterilization apparatus may be included and the sterilization may include using electrified water or water that has been exposed to ultraviolet light. The controller orients the at least one robot arm based on the dimension and/or shape determined by the at least one sensor.

15 Claims, 5 Drawing Sheets

(51) Int. Cl.
B08B 3/00 (2006.01)
A47L 15/00 (2006.01)
A47L 15/46 (2006.01)
A47L 15/22 (2006.01)
A47L 15/16 (2006.01)
A47L 15/42 (2006.01)
A47L 15/48 (2006.01)
A61L 2/18 (2006.01)
A61L 2/28 (2006.01)
A61L 2/10 (2006.01)
B25J 11/00 (2006.01)
A47K 7/04 (2006.01)
B25J 9/00 (2006.01)
A47L 15/18 (2006.01)
B25J 21/00 (2006.01)
A61L 2/04 (2006.01)
A61L 2/24 (2006.01)
G01N 21/94 (2006.01)
A61L 2/025 (2006.01)

(52) U.S. Cl.
CPC ............ *A47L 15/4295* (2013.01); *A47L 15/46* (2013.01); *A47L 15/48* (2013.01); *A61L 2/04* (2013.01); *A61L 2/10* (2013.01); *A61L 2/18* (2013.01); *A61L 2/24* (2013.01); *A61L 2/28* (2013.01); *B25J 9/0084* (2013.01); *B25J 11/0075* (2013.01); *B25J 11/0085* (2013.01); *B25J 21/00* (2013.01); *A47L 15/4236* (2013.01); *A47L 2401/04* (2013.01); *A47L 2501/30* (2013.01); *A47L 2501/36* (2013.01); *A47L 2601/06* (2013.01); *A47L 2601/10* (2013.01); *A61L 2/025* (2013.01); *A61L 2202/14* (2013.01); *A61L 2202/15* (2013.01); *A61L 2202/17* (2013.01); *G01N 21/94* (2013.01); *Y10S 901/43* (2013.01)

(56) References Cited

U.S. PATENT DOCUMENTS

| | | | |
|---|---|---|---|
| 8,523,667 B2 | 9/2013 | Clavin et al. | |
| 8,726,832 B2 | 5/2014 | Krogedal et al. | |
| 2013/0233355 A1* | 9/2013 | Alpert | A47K 10/48 134/30 |
| 2014/0067104 A1 | 3/2014 | Osterhout | |

* cited by examiner

WASHING OR WASHING/STERILIZING AND DRYING OR DRYING/STERILIZING WITH OPTIONAL INDEPENDENT STERILIZATION APPARATUS WITH ROBOTIC ARMS

FIELD OF INVENTION

The present application relates generally to apparatus and method for washing, drying and/or sterilizing objects, for example, at least one object at a time, such as a dish or hands of a person, and more particularly to efficiently, effectively, completely and quickly carrying out washing, drying and/or sterilizing the at least one object at a time.

BACKGROUND

When using a conventional dishwasher, many dishes are loaded at one time and subsequently washed and dried before being removed from the dishwasher. As dishes are cleaned, so is the dishwasher which uses water and energy resources that may be wasted. Conventional dishwashers also require a considerable amount of space, which may be disadvantageous in confined living areas such as in boats, airplanes, recreational vehicles, small houses, and office kitchens. The cycles take a long time so the dishes cannot be reused during the cleaning and drying cycle.

Both U.S. Pat. No. 7,604,012 and U.S. Patent Application No. 2013/0233355, which are incorporated in their entirety by this reference, disclose a dishwasher including embodiments for a compact dishwashing unit that is capable of washing one dish at a time.

SUMMARY OF INVENTION

The apparatus according to the present application is described with respect to a dishwasher. However, it will be appreciated that the apparatus may be used with respect to other objects, such as silverware, other cooking utensils, pots, and pans and eyeglasses. The apparatus also may be used with respect to the hands of an individual. For convenience of brevity, the apparatus will be described below with referring to a dishwasher and the object will be referred to as a dish, but it will be appreciated that the apparatus and features of the apparatus and methods described may be used with respect to objects other than or in addition to dishes, hands, and so on.

The dishwasher according to the present application is compact and configured to use substantially all of the energy resources for the desired functions of cleaning, drying and/or sterilizing. For example, the apparatus may be used to wash and to dry a dish. As another example, the apparatus may be used to sterilize the dish. Such sterilizing may be carried out while dish washing function is being carried out; while dish drying function is being carried out; while both dish washing and drying functions are being carried out; and/or separately either after a dish has been washed, or after a dish has been washed and dried, or even without the dish having been washed and/or dried. For brevity, these several features that may be included in or carried out by the dishwasher may be referred to below using the following clause or a similar clause: "wash or wash/sterilize and dry or dry/sterilize and optionally sterilize an object." It will be appreciated that these several features may be considered as alternatives, e.g., one alternative being washing and drying, another alternative being washing, drying and sterilizing, other alternatives being carrying out the sterilizing during different parts of the washing and/or drying, or another alternative being carrying out the sterilization without the dish having been washed or following the dish having been washed or following the dish having been washed and dried. Thus, for example, the features and method of the dishwasher may be described considering "at least one of" understanding, e.g., at least one of washing, drying or sterilizing, and so on. It also will be appreciated that these several features may be considered in one or more combination of functions, such as, for example, carrying functions of washing and drying or of washing, drying and sterilizing—the sterilizing being carried out, as is mentioned above, during washing, during drying, after washing, after drying, or even without the dish having been washed and/or dried.

The dishwasher may be a stand-alone unit, or built into conventional dishwashers, for example, as part of the front door of the dishwasher for rapid washing or washing/sterilization and/or drying or drying/sterilization and/or optional sterilization of an object/dish. The dishwasher may have an accordion shape for flexibility and an efficient use of a space in which the dishwasher is located which could also be useful as part of the front door of conventional dishwashers. The electricity, water and drain hook-up may be part of the conventional dishwasher. With the accordion shape, the dishwasher may also be configured to expand and retract in our out of a divider located between double sinks. Furthermore, the divider between a double sink, if made a bit wider than conventional dividers of double sinks and not expandable, could contain the dishwasher. In this case, the sink and drain hook-up may also serve as the dishwasher water and drain. The expansion in general provides the ability to store the dishwasher in a compact space. It also permits larger objects such as deep pots to be cleaned, dried or optionally sterilized which cannot typically be cleaned, dried or sterilized in conventional dishwashers. In addition, most conventional dishwashers do not sterilize objects very well. The dishwasher has multiple techniques that can be used for sterilization.

In addition to having a smaller size than conventional dishwashers, another advantage of a compact dishwashing apparatus is that the apparatus may reduce an amount of time to wash or wash/sterilize and dry or dry/sterilize and optionally sterilize an object, such as a dish. However, in reducing the amount of washing and drying time in conventional dishwashers, the dish may not be fully clean or dry. The present application is directed towards a compact apparatus that may be used to wash or wash/sterilize and dry or dry/sterilize and optionally sterilize at least one object at a time in a short time, such as on the order of seconds, by using robotic arms configured to more precisely direct at least one washing or washing/sterilizing and/or drying or drying/sterilizing apparatus/fluid and/or optional independent sterilization apparatus at the object, based on a determined dimension and/or shape of the object.

According to an aspect of the application, a washing and drying unit and/or method for washing and drying at least one object includes at least one sensor configured to determine a dimension of the object, a washing apparatus configured to direct at least one spray of at least one washing fluid to the object, a drying apparatus that may be configured to direct at least one flow of at least one drying fluid to the object, at least one robot arm connected to the washing apparatus and/or the drying apparatus, and a controller operable to orient and move the at least one robot arm. The washing and/or drying apparatus may include a fluid dispenser. The controller orients and moves the at least one robot arm based on the dimension determined by the sensor. The at least one robot arm includes at least one cleaning apparatus such as a nozzle configured to direct the spray of at least one washing fluid and/or the spray of the at least one drying fluid to the object.

According to an aspect of the application, a washing or washing/sterilizing and drying or drying/sterilizing and/or optional sterilization unit and/or method for washing or washing/sterilizing and drying or drying/sterilizing and/or optional sterilization at least one object includes at least one sensor configured to determine a dimension and/or shape of the object, a washing or washing/sterilizing apparatus configured to direct at least one apparatus/spray of at least one washing or washing/sterilizing apparatus/fluid to the object, a drying or drying/sterilizing apparatus that may be configured to direct at least one apparatus/flow of at least one drying or drying/sterilizing apparatus/fluid to the object and optionally direct at least one sterilization apparatus which may be incorporated with either the washing or drying apparatus and/or be independent, at least one robot arm connected to the washing or washing/sterilizing apparatus and/or the drying or drying/sterilizing apparatus and/or the optional sterilization apparatus, and a controller operable to orient and move the at least one robot arm. The washing or washing/sterilizing and/or drying or drying/sterilizing and/or optional sterilization apparatus may include a fluid dispenser. The controller orients and moves the at least one robot arm based on the dimensions and/or shape determined by the at least one sensor. The at least one robot arm includes at least one cleaning or cleaning/sterilizing apparatus such as a nozzle configured to direct the spray of at least one washing or washing/sterilizing fluid and/or the spray of the at least one drying or drying/sterilizing fluid to the object and/or an optional at least one sterilization apparatus.

According to another aspect of the application, the robot arm includes a first nozzle configured to direct the spray of washing fluid to the object and a second nozzle configured to direct the spray of drying fluid to the object.

According to another aspect of the application, the robot arm includes a first apparatus/nozzle configured, for example, to direct the apparatus/spray of washing or washing/sterilizing apparatus/fluid to the object and a second apparatus/nozzle configured to direct the apparatus/spray of drying or drying/sterilizing apparatus/fluid to the object and an optional third apparatus for sterilization.

According to another aspect of the application, the unit includes a support that supports the washing apparatus and/or the drying apparatus, wherein the at least one robot arm has a first end mounted on the support and a second end that contains the cleaning apparatus, wherein the second end is extendable away from the first end.

According to another aspect of the application, the unit includes a support that supports the washing or washing/sterilizing apparatus and/or the drying or drying/sterilizing apparatus and/or optional sterilization apparatus, wherein the at least one robot arm has a first end mounted on the support and a second end that contains the cleaning or cleaning/sterilizing apparatus and/or the drying or drying/sterilizing apparatus and/or optional sterilization apparatus, wherein the second end is extendable away from the first end.

According to another aspect of the application, the robot arm includes an articulated portion at the second end.

According to another aspect of the application, the robot arm is fixedly mounted to the support.

According to another aspect of the application, the robot arm is rotatably mounted to the support via a moveable base.

According to another aspect of the application, the unit includes a first and second washing apparatus and a first and second drying apparatus, wherein the first washing apparatus and the first drying apparatus are spaced apart from and facing the second washing apparatus and the second drying apparatus, allowing the object to be disposed there between.

According to another aspect of the application, the unit includes a first robot arm connected to the first washing apparatus and/or the first drying apparatus, and a second robot arm connected to the second washing apparatus and/or the second drying apparatus.

According to another aspect of the application, the unit includes a first and second washing or washing/sterilizing apparatus and a first and second drying or drying/sterilizing apparatus and/or an optional first and second sterilization apparatus, wherein the first washing or washing/sterilizing apparatus and the first drying or drying/sterilizing apparatus and/or an optional first sterilization apparatus are spaced apart from and facing the second washing or washing/sterilizing apparatus and the second drying or drying/sterilizing apparatus and/or an optional second sterilization apparatus, allowing the object to be disposed there between.

According to another aspect of the application, the unit includes a first robot arm connected to the first washing apparatus and/or the first drying apparatus, and a second robot arm connected to the second washing apparatus and/or the second drying apparatus.

According to another aspect of the application, the unit includes a first robot arm connected to the first washing or washing/sterilizing apparatus and/or the first drying or drying/sterilizing apparatus and/or an optional first sterilization apparatus, and a second robot arm connected to the second washing or washing/sterilizing apparatus and/or the second drying or drying/sterilizing apparatus and/or an optional second sterilization apparatus.

According to another aspect of the application, the controller is configured to move the first robot arm and the second robot arm independently relative to one another.

According to another aspect of the application, the at least one sensor is configured to determine an amount of cleanliness or cleanliness/sterilization of the object.

According to another aspect of the application, the sensor is configured to determine an amount of cleanliness of the object.

According to another aspect of the application, the unit includes a housing and a chamber in the housing, in which the washing apparatus and the drying apparatus are contained.

According to another aspect of the application, the unit includes a housing and a chamber in the housing, in which the washing or washing/sterilizing apparatus and the drying or drying/sterilizing apparatus and/or an optional sterilization apparatus are contained.

According to another aspect of the application, the unit includes a lift or slide mechanism configured to receive the object, lower or slide the object into the chamber, and lift or slide the object outside of the chamber, and a holder configured to hold the object in the chamber.

According to another aspect of the application, the unit includes an additional drying mechanism positioned at an outlet of the chamber, whereby the object is further dried as the object is lifted or slid outside of the chamber.

According to another aspect of the application, the unit includes an additional drying and/or sterilization and/or warming and/or cooling mechanism positioned at an outlet of the chamber, whereby the object is further dried and/or sterilized and/or warmed and/or cooled as the object is lifted or slid outside of the chamber.

According to another aspect of the application, the chamber includes openings for placing one or more hands of a person or other objects such as glasses or silverware into the chamber for washing and drying of the hands.

According to another aspect of the application, the chamber includes openings for placing one or more hands of a person into the chamber for washing or washing/sterilizing drying or drying/sterilizing and/or optional additional independent sterilization of the hands.

According to another aspect of the application, a method of washing and drying at least one object includes determining a dimension of the object to be washed, orienting and moving at least one robot arm having a cleaning apparatus based on the dimension, and directing at least one flow of at least one washing fluid and/or drying fluid at the object through the cleaning apparatus of the at least one robot arm.

According to another aspect of the application, a method of washing or washing/sterilizing and drying or drying/sterilizing and/or optional sterilization at least one object includes determining dimensions and/or shape of the object to be washed or washed/sterilized, orienting and moving at least one robot arm having a cleaning or cleaning/sterilization apparatus based on the dimensions and/or shape, and directing at least one apparatus/flow of at least one washing or washing/sterilizing apparatus/fluid and/or drying or drying/sterilizing and/or optional sterilization apparatus/fluid at the object through the cleaning, drying and optional sterilization apparatus of the at least one robot arm.

According to another aspect of the application, the method further includes determining an amount of cleanliness of the object, and one of directing the at least one flow of at least one washing fluid at the object if the object has less than a predetermined amount of cleanliness, and directing at least one flow of at least one drying fluid at the object if the object is determined to have at least the predetermined amount of cleanliness. For any areas determined not to be clean, the robotic arm may be directed to only those areas for further dry the area thus saving time, fluid and resources.

According to another aspect of the application, the method further includes determining an amount of cleanliness or cleanliness/sterilization of the object, and one of directing the at least one apparatus/flow of at least one washing or washing/sterilizing apparatus at the object if the object has less than a predetermined amount of cleanliness. For any areas determined not to be clean or clean/sterilized the robotic arm may be directed to only those areas for further cleaning or cleaning/sterilizing those area thus saving time, fluid and resources.

According to another aspect of the application, the method further includes determining whether the object is dry, and one of directing the at least one flow of at least one drying fluid at the object if the object is not determined to be dry, and stopping the at least one flow of at least one drying fluid if the object is determined to be dry. For any areas determined not to be dry, the robotic arm can be directed to only those areas for further dry the area thus saving time, fluid and resources.

According to another aspect of the application, the method further includes determining whether the object is dry or dry/sterile, and one of directing the at least one apparatus/flow of at least one drying or drying/sterilizing and/or optional sterilizing apparatus at the object if the object is not determined to be dry or dry/sterile, and stopping the at least one apparatus of at least one drying or drying/sterilizing apparatus if the object is determined to be dry or dry/sterile. For any areas determined not to be dry or dry/sterile, the robotic arm can be directed to only those areas for further drying/sterilizing the area thus saving time, fluid and resources.

As an option, according to another aspect of the application, the method further includes an optional determination whether the object is adequately sterile, and one of directing the at least one sterilization apparatus at the object if the object is not determined to be adequately sterilized and stopping the at least one apparatus of at least one sterilizing apparatus if the object is determined to be adequately sterile. Sterilization can be determined based on ultraviolet (UV) intensity and time directed at the object based on predetermined time based on previous determinations based on flow, pressure, temperature, water hardness or other relevant parameters. Alternatively, a microchip spectroscope can determine the level of sterilization of the entire object or and portions of the object. Still another method is to heat the chamber and/or water and/or air to approximately 180 degrees Fahrenheit. For any areas determined not to be adequately sterile, the robotic arm can be directed to only those areas for further sterilizing these areas thus saving time, electricity and resources.

According to another aspect of the application, the method further includes orienting a first robot arm on a first side of the object, and orienting a second robot arm on a second side of the object opposite to the first side, wherein the first robot arm and the second robot arm are oriented and moved independently relative to one another. The unit may include more than one robotic arm on each side or robotic arms on two sides, a top portion and a bottom portion of the object such that all sides, such as four sides, of the object may be cleaned.

According to another aspect of the application, the method further includes orienting a first robot arm on a first side of the object, and orienting a second robot arm on a second side of the object opposite to the first side, wherein the first robot arm and the second robot arm are oriented and moved independently relative to one another. The unit may include more than one robotic arm on each side or robotic arms on two sides, a top portion and a bottom portion of the object such that all sides, such as two, four, six or more sides, of the object may be cleaned.

According to another aspect of the application, the method further includes automatically controlling the at least one robot arm based on the determined dimension using an algorithm stored in a database in communication with a controller for controlling the at least one robot arm, determining a total time of a cycle to clean and dry the object, sending data regarding the total time of the cycle and the determined dimension to the database, and updating the algorithm based on the data received.

According to another aspect of the application, the method further includes automatically controlling the at least one robot arm based on the determined dimension and/or shape and other relevant parameters such as water and/or air temperature, water flow and/or pressure, water hardness, and environmental parameters such as ambient temperature, etc. using an algorithm stored in a database in communication with a controller for controlling the at least one robot arm, determining a total time of a cycle to clean or clean/sterilize and dry or dry/sterilize and to optionally sterilize the object, sending data regarding the total time of the cycle and the determined dimension and/or shape to the database and other relevant parameters, and updating the algorithm based on the data received.

According to another aspect of the application, the method further includes determining an amount of time to wash and dry the object, and sending data to the local processor and to a central location regarding the amount of time to wash and dry the object to the database, the dimensions of the object, environmental parameters such as the temperature of the water, ambient temperature and anything relative that can be used to improve the algorithm to maximize cleaning/drying and minimizing time to clean/dry. The central location would receive information from systems throughout the world and could then improve the algorithm continuously based on a large data set.

According to another aspect of the application, the method further includes determining the movement of the at least one robotic arm and an amount of time to wash or wash/sterilize, and dry or dry/sterilize and optionally to sterilize the object, and sending data to the local processor and/or to a central non-local location regarding the amount of time to wash or wash/sterilize, dry or dry/sterilize and optionally to sterilize the object to the database, the dimensions and/or shape of the object and/or shape and other relevant parameters such as water and/or air temperature, water flow and/or pressure, water hardness, and environmental parameters such as ambient temperature, etc., optionally the UV intensity and anything relative that can be used to improve the algorithm to maximize cleaning/drying and/or optional sterilization and minimizing time to clean/dry and/or optionally sterilize. The central location would receive information from systems throughout the world and could then improve the algorithm continuously or in batch based on a large data set and update all the systems in the field periodically.

Sterilization of the object is important in many but not all washing and drying applications. There are various levels of sterilization defined by a Sterility Assurance Level (SAL). This invention incorporates the option to not only wash and dry but to optionally sterilize an object. The sterilization can occur throughout the wash and dry cycle as, for example, when ultraviolet (UV) impacts the dish while the washing and drying are occurring. In one embodiment, fiber optics would carry the UV light so it could impinge directly on the object with maximum intensity that maximizes the sterilization in the minimum amount of time. The UV can be part of the wash and/or dry apparatus, attached to the wash and/or dry apparatus or be independent of the wash and dry apparatus. If the UV is used during the entire wash and dry cycles, it would likely not require any additional time to attain an adequate level of sterilization. Furthermore, a UV bulb in the chamber may be energized during the time the object is in the chamber to further increase the UV intensity. This could be in addition or independent of the UV that is applied to the object through fiber optics. In another embodiment, a light-emitting diode may be used instead of fiber optics. In addition, the UV could be used to sterilize the water where the water passes through a UV light before it is used to wash the object. This UV light could be the same one providing UV to the chamber or the fiber option or could be an additional UV light. Additional techniques can be employed for sterilization that can operate with the wash cycle only, the dry cycle only, with both or as an independent operation during, between or after any other cycles. For example, a technique would employ water electrolysis where hydrogen and oxygen is dissolved into the water which may include an electrolytic cell that receives water and salt which, when electrified, creates separate alkaline and acidic salt where the alkaline salt sanitizes the object. This may be incorporated only in the water wash or be used in addition to a wash that uses normal water. Still another method of sterilization would include heating the chamber and/or water and/or air to approximately 180 degrees Fahrenheit. Additional sterilization techniques may include ultrasound cleaning, other electrical techniques, other heat methods, enzymatic cleaning or any other sterilization technique.

Techniques that determine the SAL level are typically performed in a lab. The effectiveness of the sterilization using various arrangements such as water or air temperature, hardness of water, flow, pressure, etc. affect the SAL value of the different cleaning and drying techniques that are to be used and are evaluated in the lab. Based on the information available for any particular dishwasher with particular temperature, pressure and flow, purity of water, hardness of water, and/or dirt on the dish and any other relevant conditions, the algorithm could determine the time required for sterilization and where the dishwasher's sterilization is operated for that time. However, a unique technique that indicates the SAL level uses a single chip spectroscopy to determine the level of pathogens on the plate and how well they have been removed. Determining the sterilization of the object may include scanning the object with the spectroscope at random locations or the entire object. For certain health, hygiene and critical applications this can be of extraordinary importance.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

The annexed drawings, which are not necessarily to scale, show various aspects of the invention.

DETAILED DESCRIPTION

The present application is directed towards providing a washing or washing/sterilizing and drying or drying/sterilizing and/or optional sterilizing unit that may be used in a confined space. The washing or washing/sterilizing and drying or drying/sterilizing and/or optional sterilization unit is configured to wash or wash/sterilize and dry or dry/sterilize and optionally sterilize a single object, such as a dish, or a small number of objects, in one quick washing or washing/sterilizing and drying or drying/sterilizing and/or optional sterilization cycle. The washing or washing/sterilizing and drying or drying/sterilizing and/or optional sterilization unit uses robotic arms that perform the washing and/or drying and/or sterilization, allowing the washing or washing/sterilizing and drying or drying/sterilizing and/or optional sterilization unit to more efficiently wash or wash/sterilize, dry or dry/sterilize and/or optionally sterilize objects with varying, dimensions, shapes and sizes. The dimensions and/or shape of the object are detected prior to the cycle such that parameters of the cycle may be tailored to the particular object to be washed or washed/sterilized, dried or dried/sterilized and/or optionally sterilized. Examples of suitable parameters include the washing or washing/sterilizing and drying or drying/sterilizing and/or optional sterilization time, the washing or washing/sterilizing and drying or drying/sterilizing and/or optional sterilization pattern of the robotic arms, the amount of water to be used, the temperature of the water, the electricity used, the pressure or flow of the fluid or any other suitable parameters.

Figure 1:
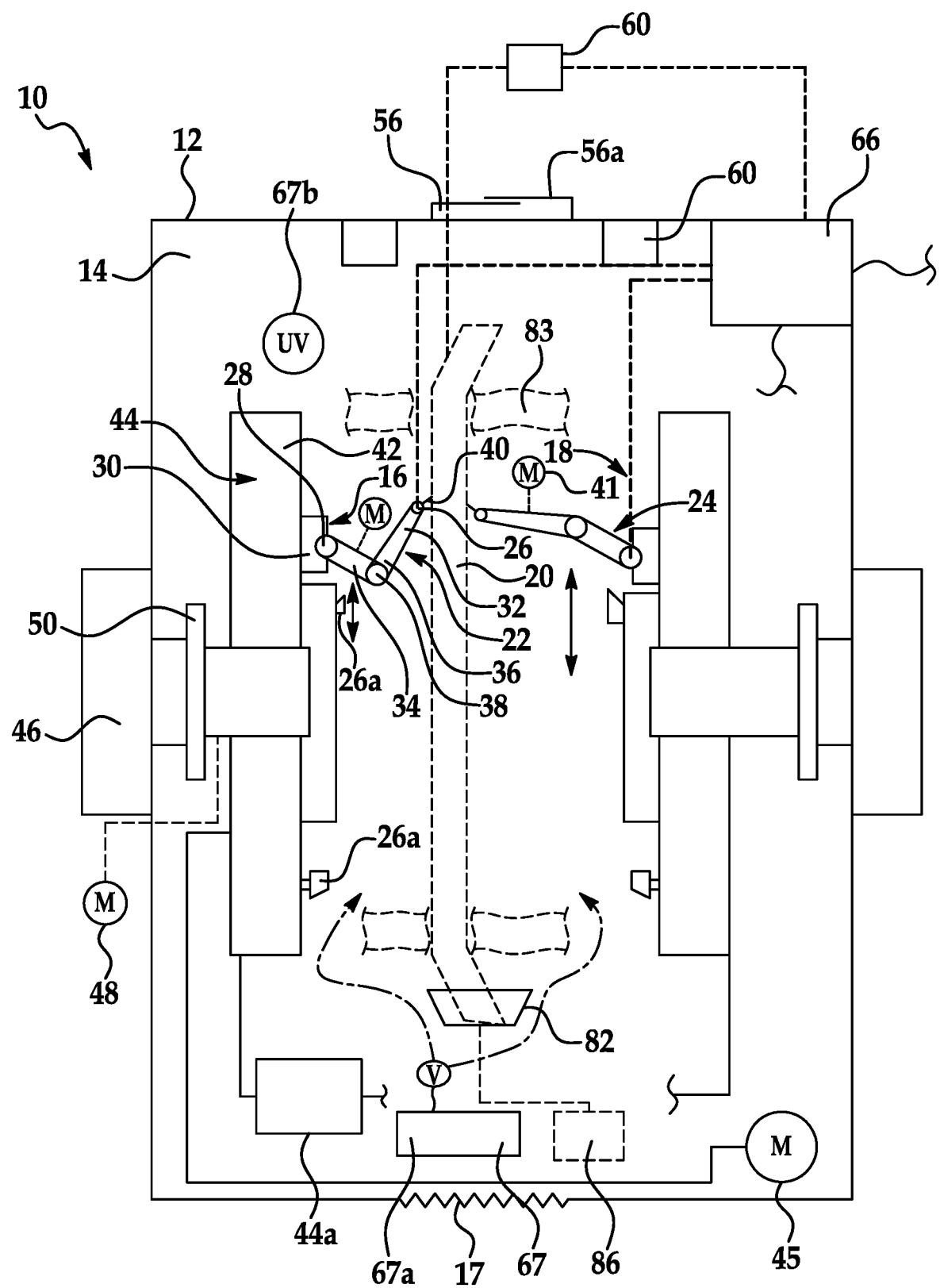
FIG. 1 is a schematic front elevation view of a washing or washing/sterilization, drying or drying/sterilization and/or optional sterilization apparatus for washing or washing/sterilizing and drying or drying/sterilizing and/or optional sterilizing an object in a chamber in accordance with an exemplary embodiment of the present application.

Referring now to FIG. 1, a washing or washing/sterilizing and drying or drying/sterilizing and/or optional sterilization unit 10 for washing or washing/sterilization and drying or drying/sterilizing and optionally sterilizing at least one object includes housing or casing 12 having a washing or washing/sterilization chamber 14 and/or an additional unit for electrifying water, in which at least one washing or washing/sterilizing and drying or drying/sterilizing and/or optional sterilizing unit 16 is contained. An outer wall 17 of the casing 12 may be configured to expand and retract such that the casing 12 of the unit 10 may be compacted when the unit 10 is not in operation, allowing storage of the unit 10 in a smaller space than when the unit 10 is in use. The outer wall 17 of the unit 10 may be accordion-shaped and when expanded, the unit 10 may have a width, for example, between approximately 5 and 18 inches or any width suitable for a particular configuration of the unit 10. The expansion can be such that pots not normally cleanable in a conventional dishwasher can be placed and cleaned or cleaned/sterilized and/or dried or dried/sterilized and/or optionally sterilized.

The chamber 14 may contain two washing or washing/sterilizing and drying or drying/sterilizing and/or optional sterilization units 16, 18 that are spaced apart to allow an object 20 to be inserted between the units 16, 18 for washing or washing/sterilizing and drying or drying/sterilizing and/or optional sterilization, a respective side of the object 20. When the unit 10 is not in use and an object 20 is not inserted, the casing 12 may be compacted into the space that the object 20 occupies when the unit 10 is not in use. The robotic arms can be designed to overlap in the stored state to further compact the unit.

The washing or washing/sterilizing and drying or drying/sterilizing and/or optional sterilization unit 10 may be configured to wash or wash/sterilize, dry or dry/sterilize and/or optionally sterilize one object at a time or a plurality of objects at a time, or in a single cycle or multiple cycles that may be performed in parallel or serially. The accordion-style casing 12 may allow more than one object 20 to be inserted within the chamber 14 for washing or washing/sterilizing and drying or drying/sterilizing and/or optional sterilization at the same time. Examples of objects that may be washed or washed/sterilized, dried or dried/sterilized and optionally sterilized by the washing or washing/sterilizing and drying or drying/sterilizing and/or optional sterilization unit 10 include dishes, bowls, pots and pans, glasses, cups, pots, pans, cookware, silverware, eyeglasses or any other suitable objects. Another example of an object that may be washed, dried and/or optionally sterilized by the unit 10 is the hands of a person.

Each washing or washing/sterilizing and drying or drying/sterilizing and/or optional sterilization unit 16, 18 may include a washing or washing/sterilizing apparatus and a drying or drying/sterilizing apparatus and an optional independent sterilization apparatus. The washing or washing/sterilizing apparatus may include a washing or washing/sterilizing apparatus/fluid dispenser and for dispensing at least one washing or washing/sterilizing apparatus/fluid as, for example, tap water, sterilized water that has been exposed to ultraviolet light and/or electrified water for improved sterilization and optional UV light from a bulb, fiber optics or other means and the drying or drying/sterilizing apparatus may include a drying apparatus/fluid dispenser for dispensing at least one drying or drying/sterilizing apparatus/fluid and optional UV light from a bulb, fiber optics, a light-emitting diode (LED), or other means. More than one apparatus/fluid for the washing or washing/sterilization and/or drying or drying/sterilization apparatus and/or optional sterilization operation may be used in the washing or washing/sterilizing and drying or drying/sterilizing and/or optional sterilization unit. The washing or washing/sterilization apparatus is configured to direct at least one apparatus/spray of at least one washing or washing/sterilization apparatus/fluid to the object 20 for washing or washing/sterilizing and optionally sterilizing the object 20 and the drying or drying/sterilization apparatus is configured to direct at least one apparatus/flow of at least one drying or drying/sterilization apparatus/fluid to the object 20 for drying and optionally sterilizing the object 20 and the optional sterilization apparatus is configured to direct at least one apparatus/flow of at least one sterilization apparatus/fluid such as electrified water or UV light to object 20 for sterilizing the object 20. The washing or washing/sterilization and drying or drying/sterilization and/or optional independent sterilization unit 10 includes at least one robot arm 22, 24 that is connected to the washing or washing/sterilization apparatus and/or the drying or drying/sterilization apparatus and/or sterilization apparatus/fluid/light.

The robot arm 22, 24 includes at least one cleaning or cleaning/sterilization apparatus, such as a nozzle 26 configured to direct the spray of washing or washing/sterilization apparatus/fluid and/or the spray of drying or drying/sterilizing apparatus/fluid to the object 20 and/or optional sterilization apparatus/fluid/light. The cleaning or cleaning/sterilizing apparatus may include a single nozzle 26 configured to direct the spray of washing or washing/sterilizing apparatus/fluid/light and the spray of drying or drying/sterilizing apparatus/fluid/light and/or optional sterilization apparatus/fluid/light. The cleaning or cleaning/sterilizing apparatus may include at least two nozzles, where one nozzle is configured to direct the spray of washing or washing/sterilization apparatus/fluid/light and the other nozzle is configured to direct the spray of drying or drying/sterilization apparatus/fluid and an optional nozzle configured to direct the spray/light for sterilization. The nozzle 26 may be rotatable about its own axis in an arrangement that is determined by the physical shape of the nozzle and/or the direction and shape of orifices associated with the respective nozzle. It should be recognized that the cleaning or cleaning/sterilizing apparatus is not limited to using a nozzle and any suitable cleaning or cleaning/sterilizing and/or drying/sterilizing and/or optional sterilization apparatus for providing a washing or washing/sterilizing and/or drying/sterilizing and/or drying or drying/ or optional sterilization apparatus/fluid and/or optional sterilization apparatus to the object may be used.

As is described further below, with reference to FIGS. 2A-3, the washing or washing/sterilization and drying or drying/sterilization and/or optional sterilization unit 10 may detect various parameters, such as dimensions and/or shape of the object intended to be washed or washed/sterilized, dried or dried/sterilized and/or optionally sterilized, cleanliness or cleanliness/sterility of the object, dryness of the object, and/or optional level of sterilization and so on. Using the dimensions and/or shape of the object allows the washing or washing/sterilization and drying or drying/sterilization and/or optional sterilization unit 10 to be controlled for effectively and efficiently washing or washing/sterilization and drying or drying/sterilization and/or optional sterilizing the object. For example, a smaller object may use less time for washing or washing/sterilization and less washing or washing/sterilization and/or optional sterilization apparatus/fluid than used for a larger object. Similarly, the smaller object may use less time for drying or drying/sterilization and less drying or drying/sterilization and/or optional sterilization apparatus/fluid than used for the larger object. Furthermore, the smaller object may use less time for optional sterilization and less use of resources in the apparatus than used for the larger object. The smaller object may use less overall resources such as electricity.

The robot arm 22, 24 may include a first end 28 mounted to a support 30 within the chamber 14. The apparatus/nozzle 26 of the robot arm 22, 24 is located at a second end 32 opposite the mounted first end 28, where the second end 32 is moveable relative to the first end 28. The second end 32 may be configured to retract towards and extend away from the first end 28. The robot arm 22, 24 may include a plurality of arms that are hinged together and configured to move relative to one another to provide multiple degrees of freedom. The robot arm 22, 24 may include a first arm 34 and a second arm 36 hinged together at a hinge 38. The hinge 38 may allow the second arm 36 to rotate, extend, and retract relative to the first arm 34, depending on a dimension and/or shape of the object 20 to be washed or washed/sterilized, dried or dried/sterilized and/or optionally sterilized. Greater degrees of freedom may be beneficial for larger objects such that the second arm 36 may extend to a maximum distance from the first arm 34 to reach an outer surface of the object 20. An articulated portion 40 at the second end 32 of the robot arm 22, 24 may also be provided for a greater precision in directing the apparatus/spray of washing or washing/sterilizing and/or drying or drying/sterilizing apparatus/fluid and/or optional sterilization apparatus at a surface of the object 20.

The washing or washing/sterilizing and drying or drying/sterilizing and/or optional sterilizing unit 10 may include a plurality of robot arms 22, 24 and each of the washing or washing/sterilizing and drying or drying/sterilizing and/or optional sterilization units 16, 18 may include at least one robot arm 22, 24. Each robot arm 22, 24 may be configured to move independently relative to another robot arm, in accordance with the dimension and/or shape of the object 20. Independently moving each robot arm allows more precise washing or washing/sterilizing and drying or drying/sterilizing and/or optional sterilizing of object having non-continuous and/or non-symmetrical shapes. For example, a bowl may have a flat bottom surface engageable with a robot arm on one side and a cup-shaped or convex surface engageable with another robot arm on an opposite side. Also, more resources may be applied to the dirtiest surface such as where food has been placed and less to the bottom of the dish which is typically cleaner to save time, resources and use resources more efficiently.

The robot arms 22, 24 may include linearly extending portions that extend towards and retract from the object 20. For example, if the object 20 to be washed or washed/sterilized dried or dried/sterilized and/or optionally sterilized is a bowl that has a primarily concave side or surface portion and a primarily convex side or surface portion. The robot arm 22, 24 positioned on the concave side of the bowl may extend further than the robot arm 22, 24 positioned on the bottom or convex side of the bowl. Providing a linearly extending and retracting portion allows the robot arm 22, 24 to more precisely direct washing or washing/sterilizing and/or drying or drying/sterilizing and/or optional sterilizing apparatus/fluid into the bowl. Each robot arm 22, 24 may be driven by a drive mechanism 41. The drive mechanism 41 may be a motor/engine, piston, or any suitable drive mechanism for driving the robot arms 22, 24 where the driving mechanism could possibly be operated by water pressure. The motor/engine may drive the robot arm 22, 24 through a gear train connected between the motor/engine and the robot arm 22, 24 to be driven. Each robot arm 22, 24 may be mounted on the respective support 30 within the chamber 14. The drive mechanism 41 may be contained within the support 30. A water driven mechanism could avoid using electricity in some applications.

The support 30 may be mounted to a unit support member 42 contained within the chamber 14 that may be part of a plenum, or reservoir 44 in which water or other fluid such as electrified water are provided for washing or washing/sterilizing the object 20. The plenum 44 may include a pump for directing water/fluid towards the apparatus/nozzle 26 during washing or washing/sterilizing of the object. The pump may be operable, for example, at a pressure of around 45 pounds per square inch and can be used to increase pressure/flow if necessary. The plenum 44 may further include a heater 44a for heating the water contained in the plenum 44. The plenum 44 may also be connected to a motor/engine 45 that drives the pump of the plenum 44 when the unit 10 is turned on for operation.

In addition to the plenum 44, a separate air plenum 46 that supplies air/drying/optional sterilization fluid for drying or drying/sterilizing the object 20 may be provided. This air may or not be heated. By way of example and not limitation, the air/drying/optional sterilization fluid plenum 46 may be located outside of the chamber 14 and include tubing and passages (not shown) within the unit support member 42 for fluid communication from the air plenum 46 towards the apparatus/nozzle 26. The apparatus/nozzle 26 may also be configured to receive water from the plenum 44 through tubing and passages in the unit support member 42. The water or air plenum 44, 46 may include additional apparatus/nozzles 26a supported on a peripheral surface of the respective plenum to provide additional washing or washing/sterilizing and/or drying or drying/sterilizing and/or optional sterilization of the object 20 during operation. The air may be combined with water to increase the energy applied to 20 during the washing or washing/sterilizing cycle. Furthermore, UV light independent and in the chamber and/or delivered through fiber optics or an LED and may be included as part of the washing/drying/sterilizing apparatus to maximize the UV intensity on the surface of the object. As part of the washing/drying apparatus the delivery would maximize the sterilization and not necessarily require additional time for sterilization.

The unit support member 42 supporting the plenum 44 may be driven by a motor/engine 48 during washing or washing/sterilizing and/or drying or drying/sterilizing and/or optional sterilization. The motor/engine 48 may include a gear train mechanism or other belt drive connection for driving a mounting structure 50 positioned within the chamber 14 that is fixed between the air plenum 46 and the unit support member 42. The unit support member 42 may be rotatable with the mounting structure 50 or fixed to the housing 12 and non-rotatable. The support 30 for the robot arm 22 may be supported on an exterior surface of the unit support member 42. The support 30 may be fixed to the unit support member 42 or movably mounted such that the support 30 may move relative to the unit support member 42. The support 30 may be configured to rotate, slide in a vertical or horizontal direction, or move in any suitable direction relative to the unit support member 42 and both the support 30 and the unit support member 42 may be rotatable. It should be recognized that in addition to the connection between the first arm 34 and the second arm 36 of the robot arm 22 and the connection between the first end 28 of the robot arm 22 and the support 30, the connection between the support 30 and the unit support member 42 provides additional degrees of freedom for the robot arm 22 to move relative to the object 20.

Figure 2A:
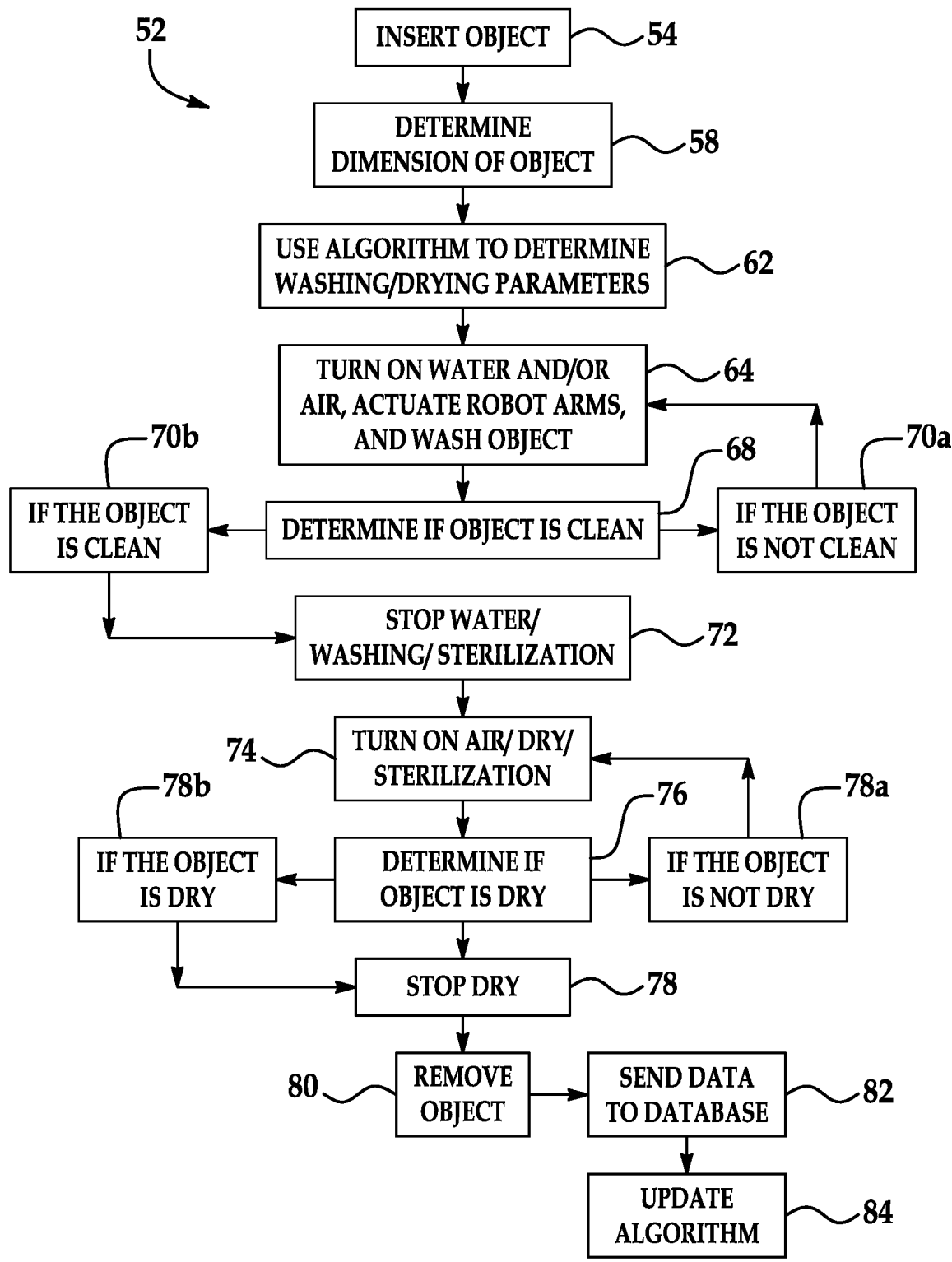
FIG. 2A is an exemplary flow chart illustrating steps for washing or washing/sterilization, drying or drying/sterilization washing and/or optional sterilization of an object using the dishwasher of FIG. 1.
Figure 2B:
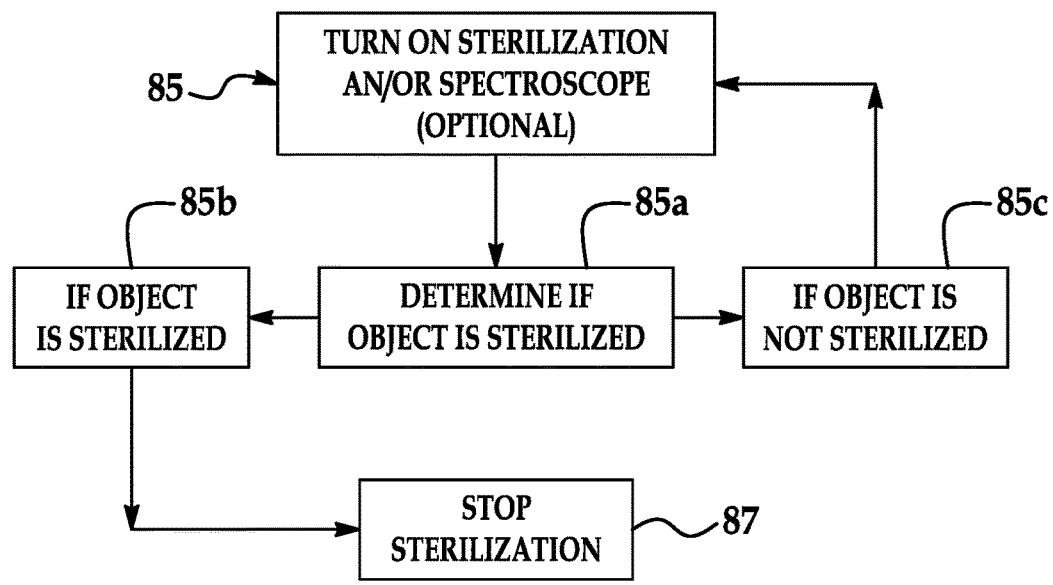
FIG. 2B is an exemplary flow chart illustrating steps for optional sterilization of an object using the dishwasher of FIG. 1.

Referring in addition to FIGS. 2A and 2B, a method 52 of washing or washing/sterilizing and drying or drying/sterilizing and/or optional sterilization the at least one object 20 is shown. Step 54 of the method 52 includes inserting the dish 20 into an entrance 56 of the chamber 14. The entrance 56 may be configured to receive a portion of the dish 20 before the dish 20 is lowered/slid (if entered through the side) into the chamber 14. As the dish is lowered/slid or once it is determined that the dish 20 is fully lowered into the chamber 14 for washing or washing/sterilizing and drying or drying/sterilizing and/or optional sterilization, step 58 includes determining a dimension and/or shape of the object 20. For example, the dimension and/or shape may include a width, height, or length and/or shape or configuration where these vary of the object 20. At least one sensor 60 may be configured to determine the dimension and/or shape and the sensor 60 may be positioned at the entrance 56 to determine the dimension and/or shape of the object 20 as the object 20 is being inserted into the chamber 14. A plurality of sensors 60 may be used for determining the dimension and/or shape and a first and second sensor or more sensors may be positioned on opposite sides and at the edges of the entrance 56 such that each of the first and second sensors is disposed on a respective side to determine the dimensions and/or shape of the object 20. The sensor 60 may include a feeler that feels the object 20 being inserted into the chamber 14, a photoelectric or optical detector, or a detector that detects any distortion of doors 56a located at the entrance 56. If distortion of the doors 56a is detected, it may be determined that the object 20 is not fully in position for the washing or washing/sterilizing and drying or drying/sterilizing and/or optional sterilizing cycle. In response to detecting distortion of the doors 56a, the washing or washing/sterilizing and drying or drying/sterilizing and/or optional sterilizing unit 10 may also be prevented from beginning the washing or washing/sterilizing and drying or drying/sterilizing and/or optional sterilizing cycle, to avoid spraying water outside of the unit 10.

Figure 3:
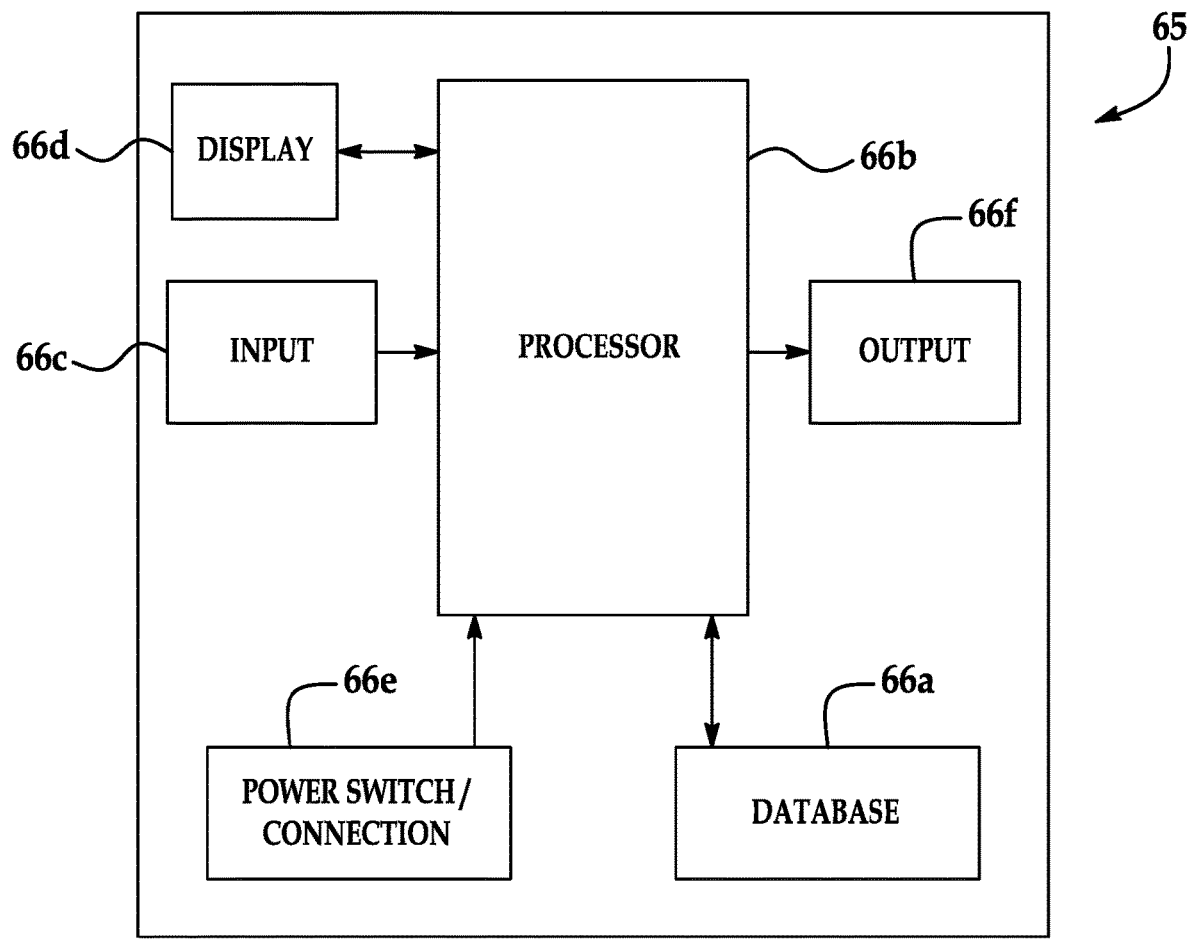
FIG. 3 is a schematic illustration of a control system for controlling a robot arm for washing or washing/sterilization, drying or drying/sterilization and/or optional sterilization of the object of FIG. 1.

Referring in addition to FIG. 3, when the dimension and/or shape of the object 20 is determined, step 62 of the method 52 includes using an algorithm to determine parameters for washing or washing/sterilizing and drying or drying/sterilizing and/or optional sterilization the object 20 based on the determined dimension and/or shape. The washing or washing/sterilizing and drying or drying/sterilizing and/or optional sterilization unit 10 may include a control system 65 for controlling the robot arms 24, 26. Examples of parameters that may be varied based on the dimension and/or shape of the object 20 include water temperature, flow and/or pressure, nozzle velocity, and the pattern or orientation of the apparatus/spray of washing or washing/sterilization and/or drying or drying/sterilization and/or optional sterilization apparatus/fluid. The algorithm may be stored in a database 66a that is in communication with a processor 66b having a controller 66 for controlling the robot arm 24, 26. The database 65 may be in wireless communication with a plurality of washing or washing/sterilizing and drying or drying/sterilizing and/or optional sterilizing apparatuses 10 and may also communicate the information to a central location not in the vicinity of the dishwasher where all data from multiple dishwashers is accumulated and processed to improve the algorithm and where the improved algorithm is downloaded to the multiple dishwashers in the field.

The processor 66b may be configured to receive from the sensor 60 an input 66c such as information about the dimensions and/or shape of the object 20. In an exemplary configuration, lasers may be used on a front side and/or edge and a first side and/or edge of the object 20 to determine the dimensions and/or shape of the object, and sensors may be used on a back side and a second side opposite the first side and/or on an edge of the first edge of the object 20 and sensors may be used on the other side and/or a second edge opposite the first edge. The object 20 may be inserted into the chamber 14 at a constant rate, such that when the laser is interrupted by the object 20, the dimensions and/or shape of the object 20 may be determined. In other exemplary configurations, ultrasound and/or radar may also be used to provide information regarding the dimensions and/or shape and/or configuration of the object 20. The processor 66b may also be configured to receive input from a display 66d and provide output to the display 66d that may be a user interface displayed on an exterior portion of the washing or washing/sterilizing and drying or drying/sterilizing and/or optional sterilizing unit 10. The processor 66b may receive an input from a user such as a number of dishes, level of dirt, or the fragility of the dishes or a start command for beginning the washing or washing/sterilizing and drying or drying/sterilizing and/or optional sterilizing cycle. The start may also be automatic when determination is automatically made that the object is completely inserted and the door closed. The user interface or display 66d may also display information to the user such as the time left in the cycle or current operation and/or other information associated with operation of the washing or washing/sterilizing and drying or drying/sterilizing and/or optional sterilizing unit 10. The control system 65 may also include a power switch connection 66d for receiving electrical power, such as through a power cord, for operating the washing or washing/sterilizing and drying or drying/sterilizing and/or optional sterilizing unit 10. The processor 66b may also be configured to provide an output 66f to the controller 66 for controlling the robot arms 22, 24. When the dimension and/or shape of the object 20 is determined, the parameters related to the dimension and/or shape are prescribed by the algorithm in the database 66a and the processor 66b is configured to output the parameters to the controller 66.

When the algorithm corresponding to the dimension and/or shape of the object is chosen by the processor 66b, step 64 includes turning on the apparatus/water and/or apparatus/air and/or optional sterilization apparatus, actuating the at least one robot arm 22, 24 and washing or washing/sterilizing the object 20 in accordance with the parameters prescribed by the algorithm. Movement of the robot arm 22, 24 is controlled by the controller 66. The controller 66 is operable to orient and move the robot arm 22, 24 and thus the apparatus/nozzle 26 associated with the robot arm 22, 24. The controller 66 may be operable to orient and move a plurality of robot arms 22, 24 independently relative to one another. An example of a pattern that the apparatus/nozzle 26 may be moved in to spray and wash the object 20 is a spiral pattern. However, it should be recognized that any suitable pattern may be used, depending on the dimension and/or shape and/or configuration of the object 20 as determined by the sensor 60. The pattern may also be determined by the amount of dirt on object 20.

The controller 66 may also be configured to control operation of the washing or washing/sterilizing and drying or drying/sterilizing and/or optional sterilization unit 10, such as the apparatus/flow of washing or washing/sterilization apparatus/fluid and drying or drying/sterilization apparatus/fluid to wash or wash/sterilize, dry or dry/sterilize and/or optionally to sterilize the object 20. During washing or washing/sterilization, a detergent and/or sanitizer and/or electrified water may also be supplied from a source 67 thereof via a valve 67a and suitable pipes, tubes, or the like. The detergent and/or sanitizer and/or electrified water may be sprayed into the chamber 14 so as to impinge on the respective surfaces of the object or dish 20 and/or to mix with water being sprayed at the dish during the washing or washing/sterilization thereof. Operation of the detergent sanitizer or electrified water device 67 and valve 67a may also be controlled by the controller 66 in a suitable cycle that may be automatic or may be selectively controlled by a user.

The object 20 may be washed and sterilized by way of water electrolysis, where hydrogen and oxygen is dissolved into water due to any method including an electric current being passed through the water or available in a reservoir that has previously been created. The washing or washing/sterilizing and drying or drying/sterilizing unit 10 may include an electrolytic cell that receives water and salt. In the electrolytic cell, electricity is applied to create separate alkaline and acidic streams. This may occur as part of the washing or washing/sterilizing cycle or between the washing or washing/sterilizing and drying or drying/sterilizing cycle or at any point during the cycle. The alkaline stream may be dispensed to wash or wash/sterilize the object 20 and the acidic stream may be disposed of outside of the washing or washing/sterilizing and drying or drying/sterilizing and/or optional sterilizing and/or optional sterilizing unit 10 or stored for later use after debris is filtered out. When the alkaline stream is sprayed or directed at the object 20, the alkaline stream reacts with the dirt on the object. Water and any suspended dirt may be easily wiped or blown away from the object. The dirt may be discarded to a trap portion of the washing or washing/sterilizing and drying or drying/sterilizing unit 10 and held in the trap portion until the trap portion is removed from the washing or washing/sterilizing and drying or drying/sterilizing and/or optional sterilizing unit 10 and is cleaned or emptied or may be stored for later use after debris is filtered out. Alternatively, the washing or washing/sterilizing and drying or drying/sterilizing and/or optional sterilizing unit 10 may include a drain positioned at a lower portion of the unit 10, where the dirt may fall due to gravitational force. The acidic portion may be later combined with an alkaline fluid to neutralize it. Neutralizing the water before the water passes through the drain may be advantageous in that damage to the drain may be prevented. The drain may discard the dirt to a location outside of the washing or washing/sterilizing and drying or drying/sterilizing and/or optional sterilizing unit 10. It should be recognized that any suitable method of storing and/or discarding the removed dirt may be implemented in the washing or washing/sterilizing and drying or drying/sterilizing and/or optional sterilization unit 10 including draining it.

Regarding sterilization functions or steps, electrified water may be used for sterilization. For example, water used to wash a dish may be electrified water. Alternatively, after having been washed, a dish may be further sprayed with electrified water. Further regarding sterilization, ultraviolet light (UV) may be directed at a dish from at least one UV source 67b for sterilization during and/or after washing, and/or during drying. The UV source 67b may be located at any suitable position within the chamber 14 or outside the chamber 14. Moreover, UV may be applied via fiber optics directed at the dish to concentrate UV at the dish or impinge directly on the dish. For example, electrified water can be used during the washing cycle and UV can be used in both the washing and drying cycle for sterilization. Applying UV through fiber optics maximizes intensity on the object and the UV can be part of both the washing or washing/sterilizing and drying or drying/sterilizing or independent. In addition, the applying of UV could be an additional independent cycle if more UV disinfectant is needed. Also, UV light can be added to the entire chamber to provide additional sterilization. In the case where the sterilization is adequate from UV alone or UV in association with electrified water and with the UV applied during the drying apparatus, no additional time for the sterilization cycles may be needed. In an exemplary embodiment, the UV source 67b may include at least one LED. Using the LED may be advantageous in that the LED may increase the intensity of UV at the dish. Another advantage of using the LED may include increasing the maneuverability of the robotic arm 22, 24 as compared with using fiber optics. The LED may also increase the reliability of the sterilization and be more cost effective to implement. Thus, it will be appreciated that sterilization is an option in the unit.

Sterilization may be accomplished by heating the chamber and/or water and/or air to approximately 180 degree Fahrenheit. Water may be run through a UV light to sterilize the water. Along with previous filtering of any debris, this feature may help in recycling the water to increase efficiency. Potential sterilization techniques include heat as described above, other heating, other electrical techniques, ultrasound and enzymatic cleaning. To monitor sterilization, a single chip spectroscope may be used. Spectroscopy may be used to determine where there is not adequate sterilization as, for example, determining the signature of non-sterilized areas. Another technique to establish adequate sterilization is the use of an external lab to determine the amount of time to reach a certain level based on flow/pressure/temperature/dirt in the dishwasher, etc. and operating the sterilization for that time based on similar conditions.

After the prescribed time of washing or washing/sterilizing occurs, as set by the algorithm, step 68 is determining if the object 20 is clean and/or optional sterilized. The at least one sensor 60 may include an additional sensor used to detect if the object 20 is clean and/or sterilized. The algorithm may include a set cleanliness or cleanliness/sterilized and/or optionally sterilization parameter against which the at least one sensor may compare a measured cleanliness or cleanliness/sterilization parameter of the object 20 to determine if the object 20 is sufficiently clean and/or optionally sterilized. Determining the cleanliness or cleanliness/sterilized of the object 20 may include measuring a reflectivity of the object 20. The sensor 60 may include an optical sensor, such as a photocell or other light sensing mechanism or spectroscopy sensor. The sensor 60 may be configured to scan areas of the object 20. If a scanned area reflects a pre-determined amount of light or the spectroscope indicates a predetermined sterilization, the object 20 may be determined to be clean and/or cleaned/sterilized and/or sterilized. If the scanned area does not reflect an amount of light equal to the pre-determined amount or the spectroscopic information does not indicate an amount of cleanliness and/or sterilization, the object 20 may be determined to need further washing or washing/sterilizing. The sensor 60 may scan various areas of the object 20 and measure the reflectivity or the spectroscope at a pre-determined number of random points of the area or the entire object 20. The fluid being discarded to the drain may also be monitored to measure the flow of debris passing through the drain, such that once the flow has less than a pre-determined amount of debris and/or sterilization, the object 20 may be determined to be clean and/or sterilized.

The fluid may be strained and cleaned as, for example, by passing the fluid through UV, and be recirculated. If the measured cleanliness or cleanliness/sterilization (if applicable) parameter of the object 20 is not at least equal to the set cleanliness or cleanliness/sterilization (if applicable) parameter, step 70a may include determining that the object 20 is not clean and/or adequately sterilized (if applicable). If the object 20 is not clean and/or adequately sterilized (if applicable), the washing and/or washing/sterilization (if sterilization is applicable) cycle or step 64 is repeated until the object 20 is determined to be clean or clean/sterilized (if applicable). The portion of the object 20 that is not clean or clean/sterilized (if applicable) may be cleaned/sterilized (if applicable) selectively to save fluid(s), resources and time. If the measured cleanliness or cleanliness/sterilization (if sterilization is applicable) parameter of the object 20 is at least equal to the set cleanliness/sterilization (if applicable) parameter, step 70b may include determining that the object 20 is clean or clean/sterilize (if applicable). If the object 20 is clean or clean/sterilized (if applicable), step 72 includes stopping the water flow through the nozzle 26 and/or the sterilization apparatus such as UV light. The cleaning or cleaning/sterilization (if applicable) apparatus/water plenum 44 and/or UV light may be turned off during step 72 such that the pump of the water plenum 44 does not continue to pump at least one fluid toward the nozzle 26 and/or the UV does not continue to emit light.

After the water flow is stopped, step 74 includes turning on the drying and/or drying/sterilization (if applicable) apparatus/air for drying and/or drying/sterilizing (if applicable) the object 20. Step 74 may include turning on the drying or drying/sterilizing apparatus/air plenum 46 such that apparatus/air/optional UV light is directed towards the nozzle 26 to be applied/sprayed at the object 20. As in step 64, movement of the robot arm 22, 24 is controlled by the controller 66 and the controller 66 is operable to orient and move the robot arm 22, 24 in accordance with the algorithm based on the dimension and/or shape determined by the at least one sensor 54. The nozzle 26 may be moved in any suitable pattern including a spiral pattern to dry the edges of 20, as prescribed by the algorithm, for drying or drying/sterilizing the object 20.

After the prescribed time of drying and/or drying/sterilization (if option is used) occurs, step 76 is determining if the object 20 is dry and/or dry/sterilized. The at least one sensor 60 may include an additional at least one sensor used to detect if the object 20 is dry and/or dry/sterilized (if option is used). The algorithm may include a set dryness and/or dry/sterilization (if option is used) parameter against which the at least one sensor may compare a measured parameter of the object 20 to determine if the object 20 is sufficiently dry and/or sufficiently dry/sterilized (if option is used). Determining the dryness or dryness/sterilizing and/or optional sterilization of the object 20 may include measuring a reflectivity or spectroscopic information of the object 20. The sensor may be a photocell or spectroscope as previously described, for scanning the object and detecting the reflectivity or spectroscopic information of the object/plate at random locations on the object or of the entire object. The drain may also be monitored for fluid passage, such that when less than a pre-determined amount of fluid passes through the drain, the object 20 may be determined to be dry and/or dry/sterilize. If the measured dryness and/or optional sterilization (if option is used) parameter of the object 20 is not at least equal to the set dryness and/or optional sterilization (if option is used) parameter, step 78a may include determining that the object 20 is not dry or adequately optionally dry/sterilized (if the option is used). If the object 20 is not dry and/or optionally dry/sterilized (if option is used), the drying and/or optional dry/sterilization (if option is used) cycle or step 74 is repeated until the object 20 is determined to be dry and/or optional dry/sterilized (if option is used). The portion of the object 20 that is not dry and/or optional dry/sterilized (if option is used) may be dried and/or optional dry/sterilized (if the option is used) selectively to save fluid, resources and time. If the measured dryness/and/or optional dry/sterilization (if option is used) parameter of the object 20 is at least equal to the set dryness and/or optional dry/sterilization (if option is used) parameter, step 78b may include determining that the object 20 is dry and/or adequately sterilized (if the option is used). If the object 20 is dry and/or optional dry/sterilized (if option is used), step 78 includes stopping the air flow and/or optional dry/sterilization (if option is used as, for example, turning off the UV light) through the nozzle 26. The air plenum 46 and/or UV light (if used) may be turned off during step 78 such that air and/or light is not directed toward the nozzle 26.

After the prescribed time of drying or drying/sterilization occurs, step 86 is determining if the object 20 is sterilized adequately, to an acceptable Sterility Assurance Level (SAL). This can be done in a laboratory setting that has predetermined the time to reach a certain SAL based on parameters such as water temperature, water hardness, flow, pressure, level of dirt or other applicable parameters and after operating for that time the operation of the unit is discontinued. Alternatively, as microchip spectroscopy has been developed, spectroscopy could be used. In applying microchip spectroscopy, an algorithm may include a set sterilization parameter as, for example, determining the signature of non-sterilized areas against which the at least one sensor may compare a measured parameter of the object 20 to determine if the object 20 is sufficiently sterilized. Determining the sterilization of the object 20 may include scanning the object with the spectroscope at random locations or the entire object. The drain may further be monitored for sterility such that when less than a predetermined amount of sterility passes through the drain, the object 20 may be determined to be sterilized. If the measured sterilization of object 20 is not at least equal to the set sterilization parameter step 86 is repeated until the object 20 is sterilized. The portion of the object 20 that is not sterilized may be sterilized selectively to save fluid, resources and time. If the measured sterilization parameter of the object 20 is at least equal to the set sterilization parameter, step 86 may include determining that the object 20 is sterilized adequately and the sterilization approaches such as UV light, ultrasound cleaning, electrified water, heat, enzymatic cleaning or any other sterilization technique is turned off. The spectroscope could also be turned off at this point.

When the drying or drying/sterilization and/or optional sterilizing cycle are complete, step 80 includes removing the object 20 from the chamber 14. During the washing or washing/sterilizing and drying or drying/sterilizing and/or optional sterilizing cycle, the object 20 may be rested on a bottom support 82 when the object 20 is inserted within the chamber 14. The object 20 may be held in a generally vertical or horizontal orientation by stabilizers 83, such as resilient or flexible flaps made of rubber or plastic, or a screen or any other method that minimizes contact with 20 and maximizes fluid flow in the chamber 14. The chamber 14 may contain a lift jack 86 that is moveable in a vertical direction through the chamber 14 and lowering the object 20 into chamber 14 or alternatively, a sliding mechanism that moves the object 20 horizontally for receiving the object 20 and sliding the object 20 into the chamber 14. During step 80, the lift or sliding jack 86 may raise or slide the object 20 through the chamber 14 such that the object 20 may be removed from the chamber 14. As the object 20 is being lifted or slid out of the chamber 14, additional blowers and/or infrared sources and/or UV and/or cooling (if the object has been heated as for sterilization) and/or other sources that improves drying or sterilizing or cooling 88 may be disposed about the entrance 56 within the chamber 14 or outside of the chamber 14. The blowers may be provided for further drying and/or cooling of the object 20. Infrared sources may be provided to warm the chamber 14 and/or the object 20 to enhance the washing or washing/sterilizing process and/or to warm the object 20 such that it is warm when it is removed from the washing or washing/sterilizing and drying or drying/sterilizing and/or optional sterilizing unit 10. The infrared sources may also heat the object 20 to enhance drying. A UV source would additionally improve sterilization. Operation of the infrared sources and/or blowers and/or UV and/or water or other devices may be controlled by the controller 67 automatically or manually by a user. Blower energy may also be combined with water energy for increased cleaning ability and reducing the amount of water required for cleaning. Combining the blower energy and the water energy may be particularly advantageous in applications where water use may be limited or restricted.

The aforementioned operation may be entirely automatic under the operation of the controller 66 or may be partly automatic and partly manually controlled by a user. Alternatively, operation may be entirely manually operated by a user that selects conditions of dirt, fragility of the object washing or washing/sterilizing and selects drying or drying/sterilizing and/or optional sterilization functions, for example. The various times for operation of the washing or washing/sterilizing and drying or drying/sterilizing and/or optional sterilization unit 10 may be varied, as desired. An example of timing may be from as little as several, such as 2 to 16 seconds, for the total operation including washing or washing/sterilizing and drying or drying/sterilizing and/or optional sterilizing It should be recognized that the timing is not limited to a particular time and will depend on the object to be washed or washed/sterilized, the number of objects, a desired amount of dryness, the desired sterilization (if applicable) and other desired parameters.

During operation of the washing or washing/sterilizing and drying or drying/sterilizing and/or optional sterilizing unit 10, locations of the robot arm 24, 26 may be periodically stored as the robot arm 24, 26 washes or washes/sterilizes and/or dries or dries/sterilizes and/or optionally sterilizes the object 20 in accordance with a path and time set by the algorithm that is prescribed based on the sensed dimension and/or shape of the object 20. After the object 20 is washed or washed/sterilized and/or dried or dried/sterilized and/or optionally sterilized (if applicable), information or data regarding the cleanliness and/or dryness and/or optional sterilization (if applicable) of the object 20 and the total time of the washing or washing/sterilizing and drying or drying/sterilizing and/or optional sterilization cycle may be determined by the at least one sensor 60. Step 82 includes using the processor 66*b* to receive and send data regarding the total time of the cycle for the object 20 and the determined dimension and/or shape and any other applicable conditions or parameters of the object 20 or of the process. The processor 66*b* may be configured to compare the data to the stored data in the database 66*a*. Step 84 includes updating the algorithm based on the data, such that parameters of the washing or washing/sterilizing and/or drying or drying/sterilizing and/or optional sterilization cycle may be adjusted for a given dimension and/or shape of the object 20 and any other applicable conditions or parameters. The algorithm may be updated by the processor 66*b* and the updated algorithm may be sent to the database 66*a* to be stored. Examples of the parameters that may be adjusted include the pattern of movement of the robot arm 24, 26, the amount of washing and/or drying spray and/or sterilization (if applicable) directed at the object 20, and the amount of time for the washing and/or drying cycle and/or sterilization (if applicable) and/or water temperature and/or water flow and/or pressure and/or other relevant parameters. The data may be sent to a central location such that information from all units or those that the user allows the data to be transmitted are amalgamated, analyzed and used to improve the algorithm on a continuous and either batched or semi-real time basis. The new algorithm is then downloaded to units in the field.

Referring now to FIG. 2B, step 85 may occur after step 74 of the method 52. Step 85 may include turning on a sterilization feature in the unit. The sterilization feature may include spectroscopy by way of a spectroscope, as described herein. Step 85*a* may include determining if the object is sterilized. Step 85*b* may include determining that if the object is sterilized, proceeding to step 87 and stopping sterilization of the object. Step 80 pertaining to removing the object from the unit may occur after step 87. If the object is determined to not be sterilized during step 85*c*, step 85 may be repeated or continued such that sterilization will occur until the object is determined to be sterilized to a predetermined value. As described herein, sterilization may occur by way of a variety of methods, including electrified water or ultraviolet methods.

Figure 4A:
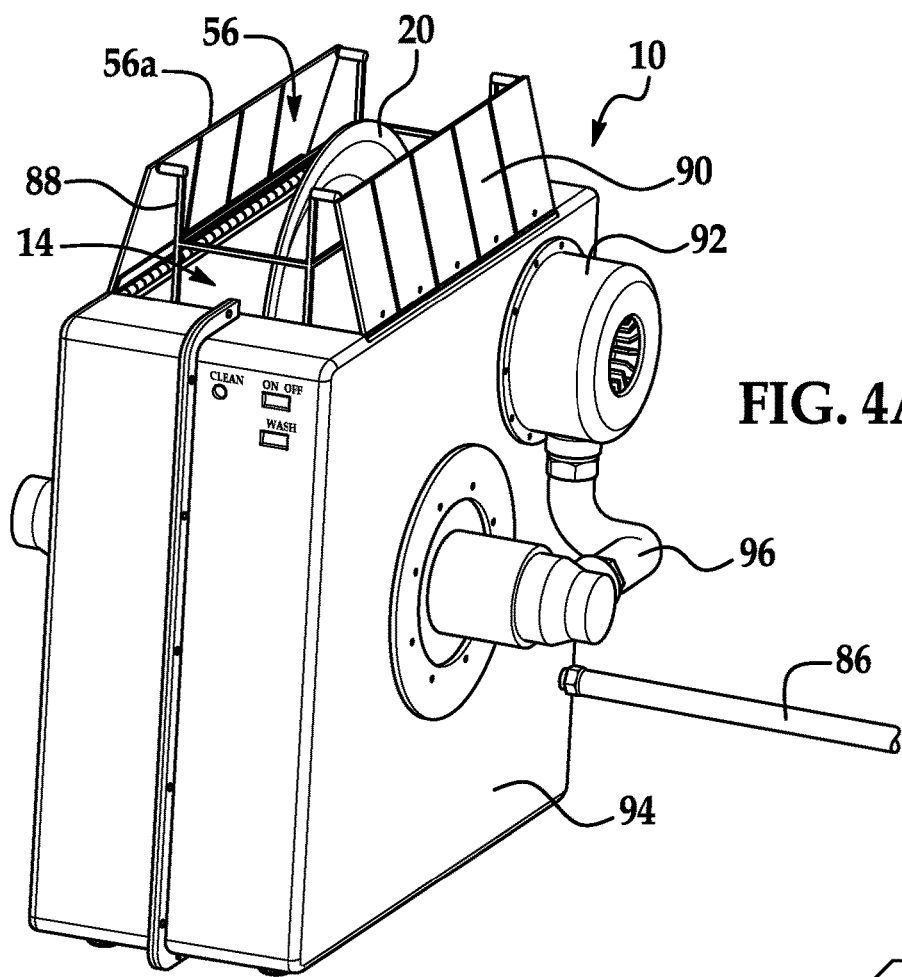
FIG. 4A is a front isometric view of a washing or washing/sterilizing and drying or drying/sterilizing and/or optional sterilization apparatus in accordance with another exemplary embodiment of the present application, showing entrance door flaps and a dish partly inserted or raised for removal from a chamber of the apparatus.
Figure 4B:
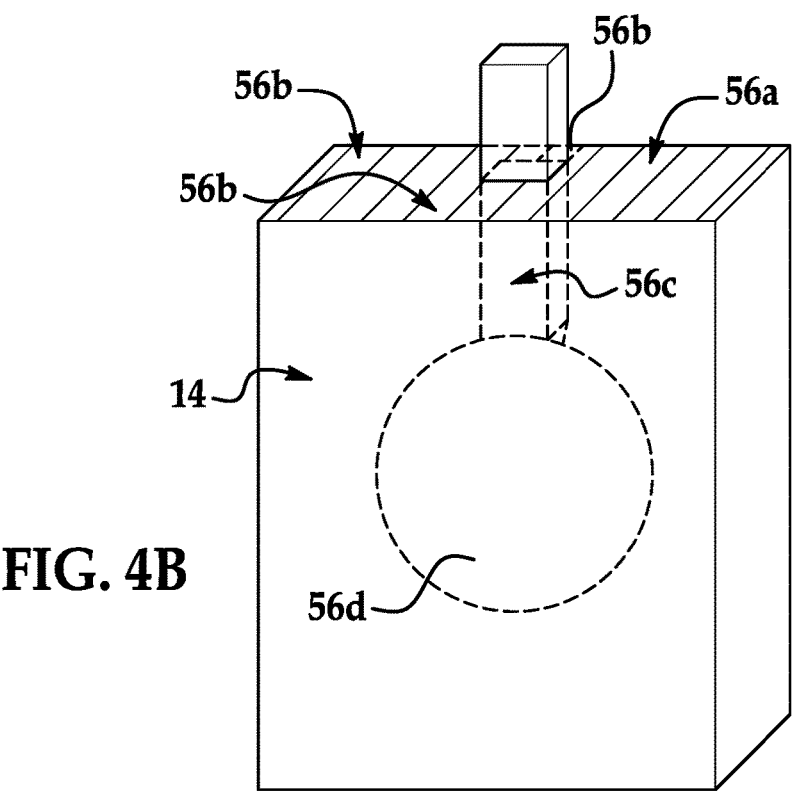
FIG. 4B is a front isometric view of a washing or washing/sterilizing and drying or drying/sterilizing and/or optional sterilization apparatus in accordance with another exemplary embodiment of the present application, showing entrance door flaps and a dish having a handle partly inserted or raised for removal from a chamber of the apparatus.

FIG. 4A illustrates an assembled view of the washing or washing/sterilizing and drying or drying/sterilizing and/or optional sterilization unit 10 for washing or washing/sterilizing and drying or drying/sterilizing and/or optional sterilization of the object 20. The washing or washing/sterilizing and drying or drying/sterilizing and/or optional sterilizing unit 10 may include a water supply tube 86 that supplies water to the plenum 44 contained within the chamber 14. The unit 10 may further include a basket 88 for supporting the object 20. Each of the doors 56*a* at the entrance 56 to the chamber 14 may define openable slots 90 through which a protrusion of an object to be washed or washed/sterilized, dried or dried/sterilized and/or optionally sterilized, such as a handle of a pan, for example, may extend during the washing or washing/sterilizing and drying or drying/sterilizing and/or optional sterilization cycle. A blower 92 may also extend from a peripheral surface 94 of the unit 10 for providing flowing air through tubing 96 toward the air plenum or unit. External chambers for water or electrified water may extend from a peripheral surface of the unit 10 for providing water or electrified water through tubing toward a plenum or to the object (not shown). The blower 92 and the tubing 96 and/or water and/or electrified water and/or other required equipment may be located outside of the chamber 14.

Referring now to 4B, the door 56*a* may be formed of incremental fingers 56*b* that allow an extending portion of the object 20, such as a handle 56*c* from a pan 56*d*, to extend outside of the chamber 14. A seal may be provided to seal the extending portion and the incremental fingers 56*b* such that fluid used in the chamber 14 does not escape from the chamber 14. The door can include rigid fingers 56*b* that rest on the handle 56*c* and a small gap may be made from the flexible fingers 56*b* that rest at an angle on the handle 56*c* such that there is no gap at a location where the fingers 56*b* attach to one another or the handle 56*c*. The fingers 56*b* may attach through some attachment device, such as magnetics. The fingers 56*b* may be mechanical devices or structures. The fingers 56*b* may be flexible and formed around the handle 56*c* using a vacuum. In another exemplary embodiment, the rigid fingers 56*b* may have a fixed portion and a portion extending from the fixed portion that rolls towards a center of the chamber 14. The rolling motion may stop when the other end of the fingers 56*b* engages another end of another finger 56*b* such that the finger ends attach, through an attachment process such as magnetics, or are stopped at an object like the handle 56*c* of the pan 56*d*.

Figure 5:
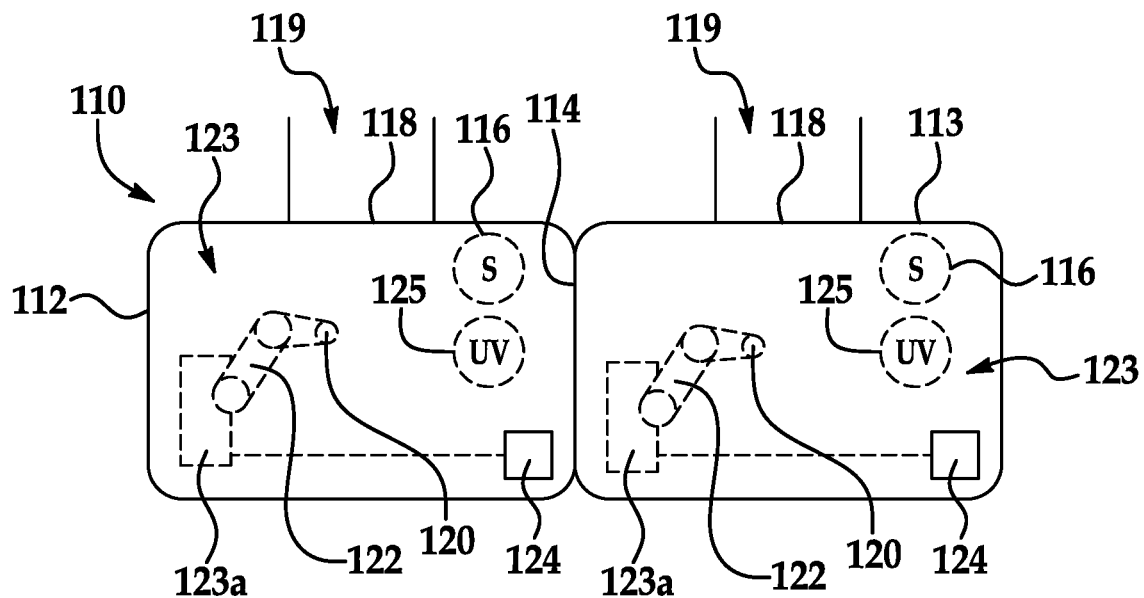
FIG. 5 is a schematic illustration of a washing or washing/sterilization, drying or drying/sterilization and/or optional sterilization apparatus in accordance with still another exemplary embodiment of the present application, showing the apparatus configured for placement of hands of person for washing or washing/sterilization, drying or drying/sterilization and/or optional sterilization of the hands.
Figure 6:
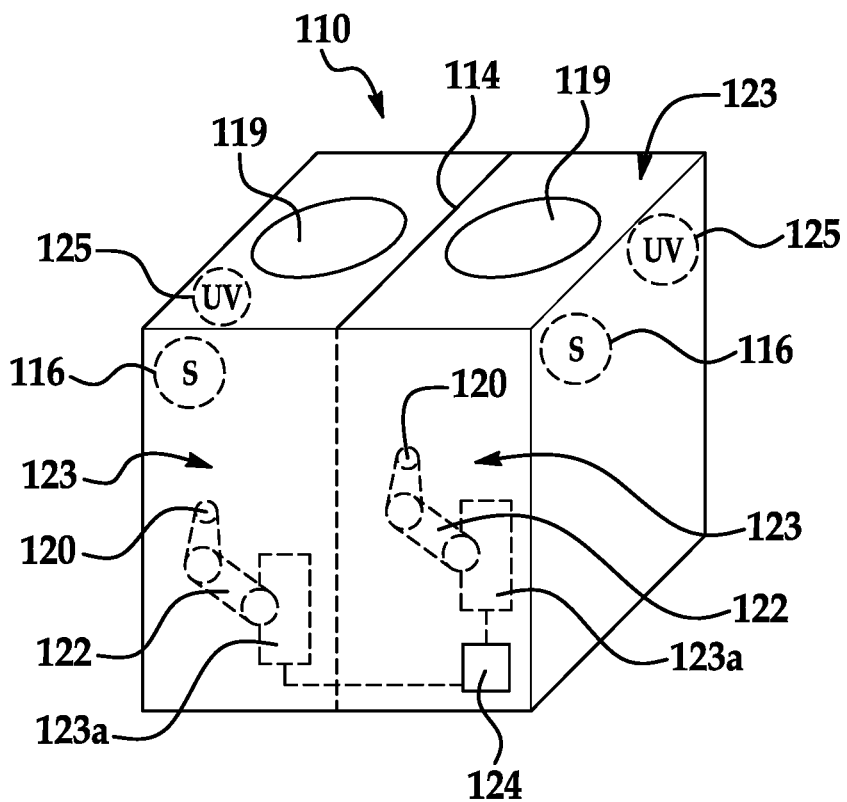
FIG. 6 is a front isometric view of the washing or washing/sterilization, drying or drying/sterilization and/or optional sterilization apparatus of FIG. 5, showing openings for placement of the hands into the apparatus.

FIGS. 5 and 6 illustrate a hand washing or washing/sterilizing and/or drying or drying/sterilizing and/or optional sterilizing system 110. The system 110 may include two separate units 112, 113 separated by a separator 114 that are similar to the washing or washing/sterilizing and drying or drying/sterilizing and/or optional sterilizing unit 10. The system 110 may be configured to wash/sterilize (if applicable) one hand at a time or more than one hand. To wash or optionally wash/sterilizing two hands, each unit 112, 113 may contain a washing or washing/sterilizing and drying or drying/sterilizing and/or optional sterilizing unit 10 for washing or washing/sterilizing both sides of both hands. For only drying or optional drying/sterilizing hands, each of the units 112, 113 may include at least one sensor 116 to sense that a person has inserted his or her hands into the entrance 118 of an opening 119, thereby to start the air flow and/or optional sterilization from the apparatus/nozzles 120 of at least one robot arm 122 to dry and optionally sterilize the hands as described above. The robot arm 122 may be mounted within a chamber 123 of the respective unit 112, 113 via a support 123*a*. The sensor 116 may be configured to turn on the washing or washing/sterilizing and drying or drying/sterilizing and/or optional sterilization cycle via controls 124. The air flow may have a more efficient drying or drying/sterilizing effect than the air flow experienced in conventional hand driers.

When the object being inserted and removed is a hand, the rate of insertion may not be constant so the dimensions of the hand are determined by various means which may include taking a picture of the hand when in the chamber or as it is being inserted and configuring the algorithm so that the washing and/or washing/sterilizing and/or drying and/or drying/sterilizing and optional sterilizing is configured so that at least one robotic arm 122 is used where at least one robotic arm 122 is configured to wash/dry and optionally sterilize each finger including each side of the finger and the sides between the fingers separately and each side of the hand serially or in parallel whichever will maximally clean/dry and optionally sterilize in the minimum time.

If the units 112, 113 are to provide both a washing or washing/sterilizing and drying or drying/sterilizing function and/or optional sterilization, the sensor 116 may sense inserting of respective hands and cause washing or washing/sterilizing and/or drying or drying/sterilization and/or optional sterilization in each of the units in a manner similar to that described above with respect to the washing or washing/sterilizing and drying or drying/sterilizing and/or optional sterilization unit 10. The configuration is advantageous in that a continuous water flow from a water faucet at a sink, and thus wasted water that is not applied to the hand(s), is not necessary for washing or washing/sterilizing hands. Furthermore, the distribution of water and also of soap and/or electrified water or other cleaning apparatus/fluid may be controlled using a control system, as previously described. The time for both washing or washing/sterilizing and drying or drying/sterilizing and/or optional sterilization is quicker for the end-user. The control system may also be configured to enable disinfecting of the hands through ultraviolet and/or electrified water or other method sources 125 in communication with the control system. The control system may also be in communication with infrared sources that may enable warming of the hands. The drying or drying/sterilizing function may begin automatically, as previously described, such that drying or drying/sterilizing begins after a sufficient amount of washing time has occurred or other adequate cleaning or cleaning/sterilization is determined. Thus, it will be appreciated that the washing or washing/sterilizing and drying or drying/sterilizing and/or optional sterilization is carried out efficiently and saves power and water and other resources because the person who is washing their hands does not have to touch any foreign objects such as a soap dispenser, water faucet, or paper towel dispenser. It is also thus more sterile.

The hand washing or washing/sterilizing and drying or drying/sterilizing and/or optional sterilizing unit is advantageous in that it enables users to make one stop for both washing and/or washing/sterilizing and drying or drying/sterilizing and/or optional sterilizing their hands. The unit may also be advantageous in enabling bathrooms to have smaller dimensions. The use of paper for drying the hands may also be reduced. The use of fluid to wash the hands may also be more efficient because the unit may be configured to provide a precise amount of fluid, in lieu of turning a faucet on and off or leaving a faucet running and dispensing water that is not used. The unit also provides a more hygienic method due to sterilization and enabling a user to wash or wash/sterilize and dry or dry/sterilize and/or optional sterilize their hands without touching a faucet or drying machine and also improve sterilization of the bathroom.

It should be recognized that the washing or washing/sterilizing and drying or drying/sterilizing and/or optional sterilizing unit 10, 110 and method has several advantages over conventional dishwashing devices. For example, using the controller to control the robot arms having articulated portions allows more precision in controlling the washing or washing/sterilizing and drying or drying/sterilizing and/or optional sterilization of an object based on the dimensions and/or shape of the object, and also decreases the total time of completion of the washing or washing/sterilizing and drying or drying/sterilizing and/or optional sterilization cycle permitting more efficient operation, using less resources where all the resources are focused on the task of cleaning the desired object and not the apparatus that is enclosing them as occurs in standard dishwashers. Another advantage is that the accordion-style casing allows the apparatus to be stored and accommodate less space when not in use, allowing the apparatus to be well-suited for a recreational vehicle, boat, airplane, small home, or office kitchen. The accordion-style casing may also allow more than one object to be washed and dried during a single washing or washing/sterilizing and drying or drying/sterilizing and/or optional sterilizing cycle such as glasses or silverware. Still another advantage is that using a database that is in communication with the washing or washing/sterilizing and drying or drying/sterilizing and/or optional sterilizing apparatus and stores an updateable algorithm ensures efficiency of the apparatus that continuously improves. The apparatus is also configured to accommodate objects of different and highly variable sizes and shapes, such as deep pots, some of which cannot be accommodated in standard dishwashers.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A washing and drying unit for washing and drying at least one object, wherein the unit is configured for at least one of washing, drying, and sterilizing, or any combination thereof, the unit comprising:
   at least one sensor configured to determine a dimension and/or shape of the object;
   a main apparatus configured for at least one of washing, drying or sterilizing the object;
   at least one robot arm connected to the main apparatus, wherein the at least one robot arm is configured to direct a washing or drying or sterilization fluid at the object; and
   a controller operable to orient and move the at least one robot arm, wherein the controller orients the at least one robot arm based on the dimension and/or shape determined by the at least one sensor.

2. The unit according to claim 1, wherein the at least one robot arm includes at least one cleaning and/or sterilizing apparatus configured to direct a cleaning and/or sterilizing spray at the object.

3. The unit according to claim 1, wherein the at least one robot arm includes at least one drying and/or sterilizing apparatus configured to direct a drying and/or sterilizing spray at the object.

4. The unit according to claim 1, further comprising a sterilization apparatus that is operable independent from the main apparatus.

5. The unit according to claim 1, wherein the at least one robot arm includes a first robot arm apparatus for washing and/or sterilizing and a second robot arm apparatus for drying and/or sterilizing.

6. The unit according to claim 5, wherein the first robot arm apparatus includes another apparatus or nozzle configured to direct a cleaning and/or sterilization apparatus or spray to the object, and wherein the second robot arm apparatus includes another apparatus or nozzle configured to direct a drying and/or sterilization apparatus or spray to the object.

7. The unit according to claim 1, further comprising a support that supports the main apparatus and/or a second apparatus, wherein the at least one robot arm has a first end mounted on the support and a second end that contains the main apparatus and/or the second apparatus, wherein the second end is extendable away from the first end.

8. The unit according to claim 7, wherein the at least one robot arm includes an articulated portion at a distal end.

9. The unit according to claim 7, wherein the at least one robot arm is fixedly mounted to the support or rotatably mounted to the support by a moveable base.

10. The unit according to claim 1, further comprising a sterilization apparatus configured for sterilizing the object with sterilized water that has been exposed to ultraviolet light and/or uses electrified water.

11. The unit according to claim 1, wherein the at least one sensor includes a spectroscopy sensor, wherein the spectroscopy sensor is configured to scan areas of the object and if a scanned area has a non-sterilized signature, the spectroscopy sensor indicates a predetermined amount of sterilization.

12. The unit according to claim 1 further comprising:
   a housing and a chamber in the housing, in which the main apparatus is contained;
   a lift or sliding mechanism configured to receive the at least one object, lower/slide the at least one object into the chamber, and lift/slide the at least one object outside of the chamber; and a holder configured to hold the at least one object in the chamber.

13. The unit according to claim 12, further comprising an additional drying and/or sterilization mechanism positioned at an outlet of the chamber, whereby the at least one object is further dried and/or sterilized and/or heated and/or cooled as the at least one object is lifted or slid outside of the chamber.

14. The unit according to claim 12, further comprising at least one door at an entrance to the chamber, wherein the door includes openable slots through which a protrusion of an object to be washed may extend, wherein the at least one door includes fingers that rest on the protrusion of the object, the fingers being flexible to rest on the protrusion at an angle, the fingers being engageable with one another.

15. The unit according to claim 12, wherein the chamber includes openings for placing one or more hands of a person into the chamber for at least one of washing, drying, and sterilizing, or any combination thereof.

* * * * *